United States Patent [19]
Stern

[11] Patent Number: 5,437,611
[45] Date of Patent: Aug. 1, 1995

[54] DYNAMIC BRACE JOINT

[75] Inventor: Elliot L. Stern, Auburn, Ala.

[73] Assignee: Orthotic Rehabilitation Products, Inc., Tampa, Fla.

[21] Appl. No.: 160,389

[22] Filed: Dec. 1, 1993

[51] Int. Cl.$^6$ .............................................. A61F 5/00
[52] U.S. Cl. ...................................... 602/16; 602/26; 482/124
[58] Field of Search ................... 602/5, 16, 26, 20, 23; 16/337, 342; 482/121, 124

[56] References Cited

U.S. PATENT DOCUMENTS

| | | | |
|---|---|---|---|
| 4,433,679 | 2/1984 | Mauldin et al. | 602/26 X |
| 4,817,588 | 4/1989 | Bledsoe | 602/16 |
| 4,846,842 | 7/1989 | Connolly et al. | 602/26 X |
| 4,865,024 | 9/1989 | Hensley et al. | 602/26 X |
| 4,982,732 | 1/1991 | Morris | 602/26 X |
| 5,036,837 | 8/1991 | Mitchell et al. | 602/26 X |
| 5,052,379 | 10/1991 | Airy et al. | 602/16 |
| 5,116,296 | 5/1992 | Watkins et al. | 602/26 X |

Primary Examiner—Linda C. M. Dvorak
Attorney, Agent, or Firm—Laff, Whiteset, Conte & Saret, Ltd.

[57] ABSTRACT

A dynamic brace joint for use in orthotic devices which adjustably restrains and limits the flexion and extension range of a limb joint while promoting and assisting joint extension or flexion using a continuously applied, adjustable, dynamic force. The dynamic brace joint includes an upper brace support member and a lower brace support member, which are pivotally interconnected at their proximal ends. The joint may be incrementally adjusted to provide a range of pivotal motion between the interconnected upper and lower members. A tensioning, elastic, or resilient member exerts a continuously applied adjustable dynamic force on the interconnected upper and lower members. The terminal end of the brace support members may be incorporated into a splint or brace to accommodate limb parts associated with the limb joint.

22 Claims, 2 Drawing Sheets

DYNAMIC BRACE JOINT

FIELD OF THE INVENTION

This invention relates to dynamic brace joints for use in orthotic devices. More particularly, this invention relates to articulated splints and braces for treating contracture and other rehabilitative conditions.

BACKGROUND OF THE INVENTION

There are many braces for the protection, orthosis, and rehabilitation of limb joints in the human body. Such braces are diverse and may be used for a variety of purposes, which include: protecting against injury due, in particular, to transverse impact; rigidly limiting or restricting the normal range of motion; providing joint control due to instability; and assisting in the rehabilitation and mobilization of the joint. Generally, these braces are most effective in joint orthosis when the normal motion of a joint on a human limb is duplicated or accommodated by the brace, without restriction in order to minimize or avoid undue stress or strain within the joint. Accordingly, braces are most readily applied to synovial joints and are predominantly of the hinge variety. The joints in such braces often provide articulated motion by any one of many means such as, for example, single axis revolutes, bipivotal hinges, cam actuations, or "free form" controls furnished by multi-directional, flexible members.

Numerous U.S. patents illustrate a variety of brace joint designs and their unique functionality as related and applied to a specific medical application. For example, each of the U.S. Pat. Nos. 4,817,588 and 4,982,732 discloses a single axis hinged brace joint for injury recovery or limited post-operative restraint which include an adjustable, angular range of motion by means of flexion and extension stops that may be locked into place. In addition, the U.S. Pat. No. 4,982,732 discloses a keyed lock which prevents tampering with the brace joints.

U.S. Pat. Nos. 4,688,559 and 5,018,514 disclose a hinged and polycentric joint, respectively, which are designed to duplicate the more complex rolling and sliding behavior of the human knee during flexion and extension while simultaneously providing joint stability and limiting the forces of variable magnitudes to prevent abnormal rotations. Additionally, the '559 patent employs a tension cable and cam surfaces which provide the patient with a means for aligning and fixing the joint.

U.S. Pat. No. 4,100,918 discloses a dynamic knee extension assist for use by paraplegics or patients without adequate muscular structure and includes an elongated plastic cord with means for making tension adjustments. Moreover, the '918 brace provides a controlled knee for assistance, particularly in rising from and descending into a sitting position. Likewise, a similar concept for a knee and elbow brace joint is described in one of the embodiments of U.S. Pat. No. 4,433,679. In the '679 patent, several brace joint designs are disclosed for providing stabilization and rehabilitation for the knee or elbow.

U.S. Pat. No. 4,838,251 discloses a dynamic knee brace which utilizes an elastic member as a resilient return means and involves a method for working muscles which, in part, allows the patient to sit normally. The elastic member described in the '251 patent is eccentrically located with respect to the joint hinge which provides a moment about the pivot when the elastic member is in tension due to a flexion of the knee. Essentially, the joint function, which is about the same as the joint function shown in the '251 patent, is disclosed in U.S. Pat. No. 4,657,000 wherein an adjustable splint includes a compression spring that may be axially preloaded against a cam surface to provide an eccentrically applied force.

Although the aforementioned U.S. patents illustrate a variety of joint designs for braces and splints, there are problems associated with their designs. For example, the known brace joints have limited functionality. Specifically, the known joint designs either include means for adjusting the tension force or the range of angular motion within the splints and braces.

Accordingly, an object of the present invention is to provide a new and improved compact dynamic brace joint design for use in orthotic devices which overcomes the above-described design limitations. In particular, an object is to provide a brace joint that includes both a quantifiable continuous force and an incrementally adjustable range of angular motion that is controlled by flexion and extension limits.

SUMMARY OF THE INVENTION

In keeping with an aspect of the invention, these and other objects are accomplished by a dynamic brace joint for use in orthotic devices and, in particular, articulated splints and braces. The inventive brace joint provides a useful treatment for contracture and includes a compact, slim line brace joint that is specifically applicable to splints and orthotic braces used for predominantly hinged joints of limbs.

The application of the dynamic brace joint provides a single axis revolute motion. In particular, the dynamic brace joint provides a quantifiable continuous force over a range of motion which may be incrementally adjustable. The design of the dynamic brace joint includes inherent attributes which promote the proper use of the joint, a method of preventing the patient from tampering with the desired range of motion, and means for adjusting the magnitude of the force even while in use. The dynamic brace joint additionally provides preventive and corrective extension load treatment for therapy and rehabilitation of contracture conditions which include but are not limited to skin and joint contracture, deformity, or deviation due to stroke, paralysis, muscle, tendon, or nerve injury resulting from a burn, injury, or lack of use.

BRIEF DESCRIPTION OF THE DRAWINGS

A preferred embodiment of the invention is shown in the attached drawings, wherein.

DETAILED DESCRIPTION OF THE INVENTION

The inventive dynamic brace joint may be employed as brace for the ankle, knee, elbow, wrist, and fingers. Hence, while the dynamic brace joint is described herein as a knee brace, it is not limited to the application of a dynamic knee brace, but may be applied to any suitable joint.

The knee brace may use a pair of the dynamic brace joints positioned on both the medial and lateral sides of the knee and is essentially symmetric with respect to the paramedian plane. Therefore, the following specification is limited to a description of one upper and one lower brace support member interconnected by a single dynamic revolute joint, the support for the opposite of the knee being essentially a mirror image of the support described herein.

The upper brace support member and the associated joint components which are adjustably fixed to and rotate with the upper brace member are herein identified and referred to by the word "femoral". The lower brace support member and the corresponding joint components are herein identified and referred to by the word "tibial".

Figure 1:
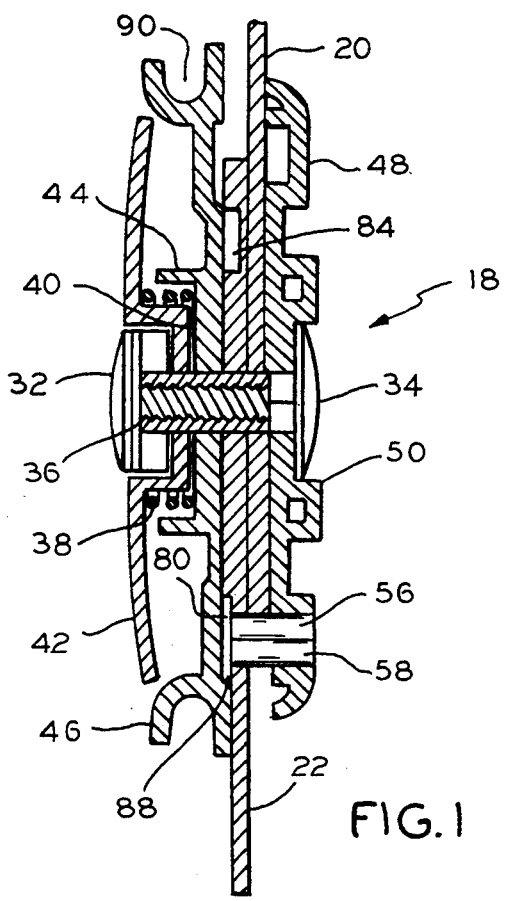
FIG. 1 is a partial vertical cross-sectional view of the assembled joint (without either an elastic member or a complete brace support members)

FIG. 1 shows an assembled dynamic brace joint 18 for adjustably restraining and limiting the flexion and extension range of the motion of a limb joint while continuously promoting and assisting joint extension. Joint 18 has an upper brace support member 20 and a lower support member 22 which are pivotally interconnected at their proximal ends, 24 and 26, respectively. Members 20, 22 are preferably made of a strong metal such as hardened aluminum or steel plates. Soft upper and lower cuffs (not shown) are removably slipped over and fixed to the elongated ends 28, 30 of the brace members in order to embrace and accommodate limb parts which are interconnected by the limb joint. Slot 31 provide means for attaching the members 28 to a limb.

Figure 4:
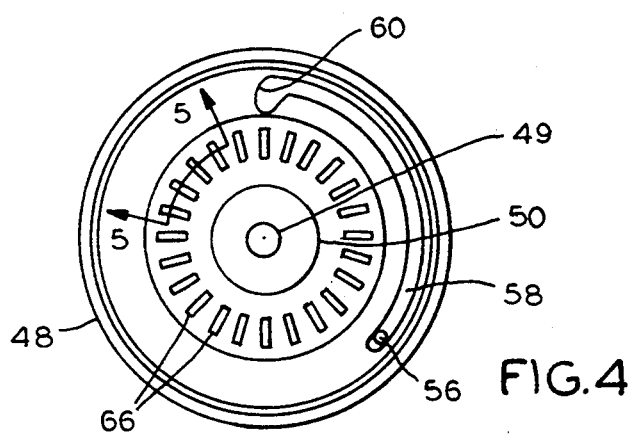
FIG. 4 is a plan view of a femoral cap which may be set in order to fix an excursion of a patient's joint.

FIG. 1 illustrates a vertical cross-sectional view of the assembled hinge brace joint 18. The revolute axis of rotation of brace joint 18 corresponds to the centerline of a screw assembly 32, 34 forming an axis around which the femoral member 20 and the tibial member 22 rotate. The screw assembly includes a male screw 32 and a corresponding threaded female post 34. A ramp washer 36 is permanently fixed to the washer face of the screw head. Femoral member 20 and tibial member 22 are given a spring bias by a coiled spring 38 nestled in a space formed at 40 on locking cap 42 and at 44 on tibial cap 46. Hub bushings and TEFLON (polytetrafluoroethylene) plate bushings may be employed to provide a mutually free rotation of the femoral and tibial members, 20 and 22, respectively. Femoral cap 48 fits axially over female post 34 which passes through the cap's center hole 49 (FIG. 4). Femoral cap 48 contains a circular inset 50 which recesses the female post head.

Figure 3:
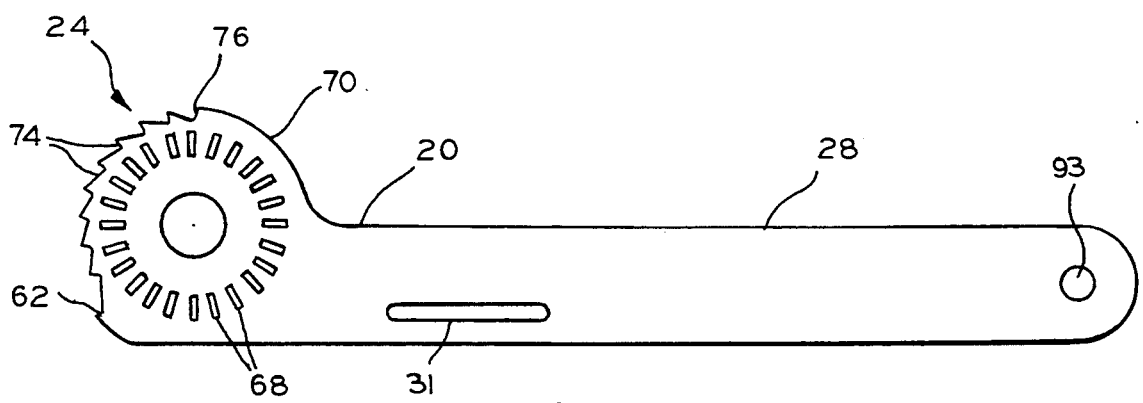
FIG. 3 is an elevation view of the femoral brace member.

Femoral cap 48 (FIG. 4) controls the brace joint's range of motion via a floating stop pin 56 which travels in an arcuate pin control slot 58. That is the excursion of pin 56 is within an arc of pin control slot 58 which extends from a stop end 60 of the slot 58 itself to a flexion stop end 62 (FIG. 3). The relative orientation of the femoral cap 48 with respect to the femoral member 20 causes the pin to be guided into cove 64 engaging the pin 56 with a flexion pin stop 74. Formed in control slot 58 to provide a femoral termination is cove 64 (FIG. 4) which extends inwardly from flexion stop end 60 and is partially radially oriented to receive pin 56 at the end of its excursion. Since floating stop pin 56 is subjected to significant shear loads, it is made from a sufficiently strong material, such as stainless steel.

Figure 5:
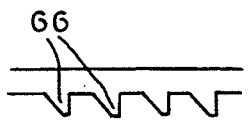
FIG. 5 is a partial cross-sectional view of the femoral cap teeth, taken along line 5—5 of FIG. 4.

Numerous upstanding, radially oriented teeth 66 may be formed on femoral cap 48 and arranged in a circular pattern centered on center hole 49. Teeth 66 are separated by about 15 degree increments (FIG. 5) to project away from the flat side surface.

Femoral member 20 (FIG. 3) has a plurality of radially oriented slots 68 arranged in a circular pattern centered on the center hole 67. Slots 68 are spaced at about 15 degree increments. The geometry is such that the teeth 66 on femoral cap 48 may be fitted into the slots 68 on femoral member 20, with members 20, 48 being in virtually any radial position allowed by the 15° separation between teeth 66 and slots 68. Thus the amount of rotation of the brace depends upon the arcuate distance between stop end 60 on control slot 58 and stop end 62 on member 20, and that distance, in turn, depends entirely on the mutual positions selected when the teeth 66 on cap 48 are pressed into the slots 68 on member 20. For example, the cap teeth 66 may be fitted into the slots 68 so that stop ends 60, 62 are separated by 15° in which the pivotal motion between arms 20, 22 is limited to the 15° travel permitted to pin 56 in arcuate slot 58. If the assumption had been that teeth 66 had been fitted into slots 68 with, say, an arc of 45° between stop ends 60, 62, the pivotal motion between arms 20, 22 would be 45°. In like manner, almost any suitable angle may be selected with in the length of the arcuate slot 58.

Femoral member 20 has a head section 70 and an arm section 28. Arm section 28 contains one or more longitudinal slots which may receive and fix the soft femoral cuff that fastens the brace member 20 to the leg. A series of equally spaced peripheral teeth are located on head section 70 of femoral member 20 and comprise pin stops 74.

Figure 2:
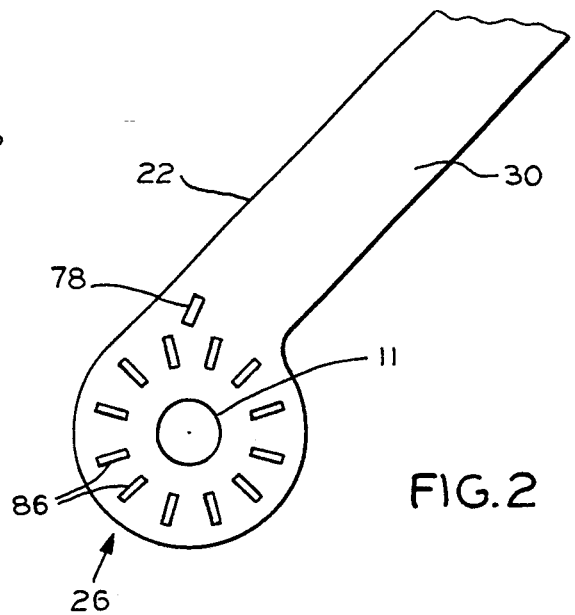
FIG. 2 is a partial elevation view of the tibial brace member.

Floating stop pin 56 is placed through a stop pin drop slot 78 (FIG. 2) in the tibial member 22. Additionally, pin 56 passes into pin control slot 58 (FIG. 4) of the femoral cap 48. Floating stop pin 56 includes a head 80 (FIG. 1) which has a diameter greater than the width of the stop pin drop slot 78. The floating pin stops the angular movement of the arms 20, 22 by engaging stop end 60 when angular movement is in one direction and stop end 62 when movement is in the other direction.

Center hole 82 of a plastic tibial cap 46 (FIGS. 1, 6, and 7) is placed on female post 34. A plurality of radially oriented teeth 84 (FIG. 7) are equally spaced at 30 degree increments and in a circular pattern centered geometrically, on hole 82, teeth 84 correspond to a plurality of tibial cap slots 86 (FIG. 2) which are also arranged in a circular pattern of 30° increments and centered on hole 87. The head of floating stop pin 56 fits into an angular tibial cap recess 88.

Figure 10A:
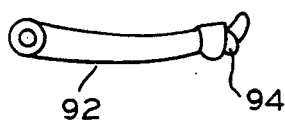
FIG. 10A and 10B are partial views of an elastic member depicting proximal end alternatives, which cooperates with the tibial cap to apply the elastic bias.
Figure 10B:
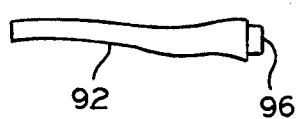

Tibial cap 46 has a circumferential groove 90 in which an elongated tension, elastic or resilient member 92 (FIG. 10A and 10B) is wound to provide a means of exerting an adjustable force which continuously applies a resistance to flexion while promoting and assisting extension. Specifically, the elastic member 92 provides a dynamically varying force which increases proportionally with the degree of knee flexion. One preferred embodiment of the tension, elastic or resilient member 92 is a thick-walled surgical tubing with a circular cross section.

Figure 6:
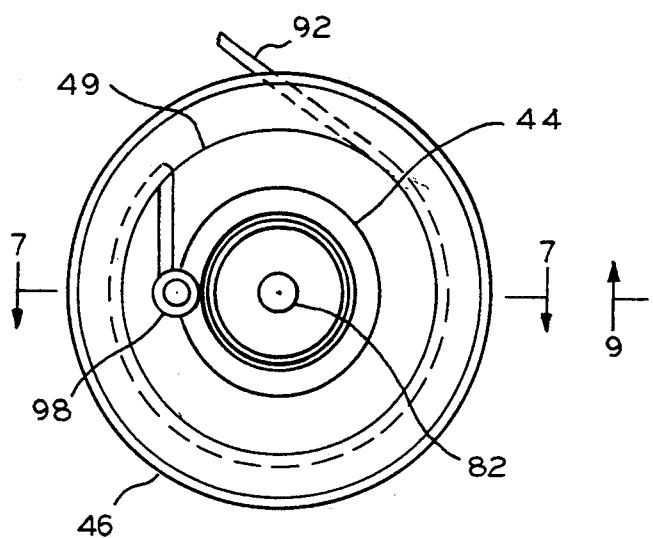
FIG. 6 is a plan view of the tibial cap which controls an elastic bias applied to the joint.
Figure 7:
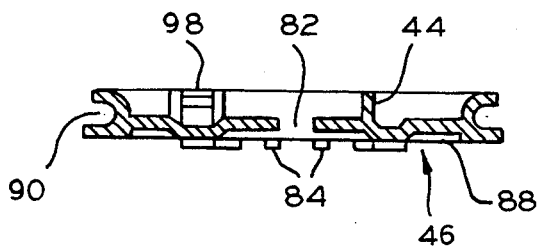
FIG. 7 is a cross-sectional view of the tibial cap, taken along lines 7—7 of FIG. 6.

The distal end of the tension elastic or resilient member 92 may be attached to the distal end of member 20, for example, attached to a hole 93 (FIG. 3). The proximal end of the tension, elastic or resilient member 92 may be knotted at 94 (FIG. 10A) or may contain an internal plug 96 (FIG. 10B) which significantly increases the diameter of the tubing so that it may be attached to tibial cap 46 by passing through a recess 98 in groove 90 (FIG. 6). The tension elastic member 92 may lie in the groove 90 and be wrapped around any selected arcuate dimension of the circumference of tibial cap 46. Then, with the selected amount of wrap in place, teeth 84 (FIG. 7) are pressed into slots 86 on member 22 in order to fix the position of the tibial cap 40 relative to the tibial member 22.

If the elastic member 92 is wrapped around a large arcuate distance in groove 90 before teeth 84 are pressed into slots 86, the elastic member 92 has great tension. If the wrap is around a small arcuate distance in groove 90, the member 92 has a small tension. Hence, the members 20, 22 may be given any suitable and selected mutual spring-like bias relative to each other in order to resist or promote their mutual arcuate movement by this simple expedient of selecting the amount of arcuate wrap given to elastic member 92 before the tibial cap 46 is attached to tibial member 22.

Figure 8:
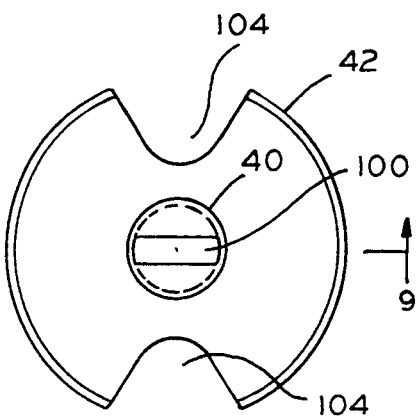
FIG. 8 is a plan view of the locking cap which protects other parts.
Figure 9:
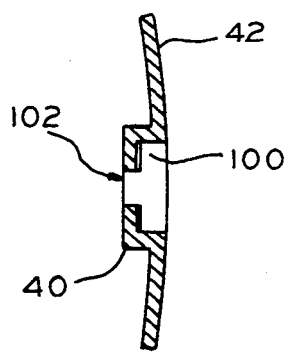
FIG. 9 is a cross-sectional view of the locking cap, taken along line 9—9 of FIG. 8.

A plastic locking cap 42 is shown in FIGS. 1, 8, and 9. A coil spring receiving cup 40 (FIG. 9) cooperates with a circular wall 44 (FIG. 7) to form a space for receiving and enclosing the coil spring 38 (FIG. 1). Male screw 32 (FIG. 1), with its permanently attached ramp washer 36, is inserted through a keying slot 100 and hole 102 (FIGS. 8, 9) of the locking cap 42. The coil spring 38 is compressed to provide a selected spring bias, as required by tightening the screw assembly 32, 34. The heads of both the screw 32 and post 34 contain a transverse "nickel" slot to facilitate initial fastening during assembly, perhaps with a coin being used as the screw driver. Additionally, the screw assembly 32, 34 may be tightened by rotating the locking cap 30 by utilizing the finger slots 104, 104 (FIG. 8).

The range of arcuate motion of the brace members 20, 22 is set by selecting the distance between end stops 60, 62, and therefore the effective length of slot 58, prior to placing the brace on the patient's limb. This range of arcuate motion may be set in any suitable angular limits provided by the 15 degree graduations of teeth 66 (FIG. 4) and slots 68 (FIG. 3), without requiring the use of tools. Although the dynamic joints of the brace placed on opposite sides of the knee are normally set for the same flexion limit (which results in a default extension limit of 180 degrees), the design permits the dynamic joints to be independently set to different limits providing both flexion and extension stops within the range of motion. Thus, it is conceivable to set the joint so that the knee may bend between say, 60 and 90 degrees.

The range of motion is readjusted by partially unscrewing the locking cap 42 and therefore screw 32. By depressing the head of screw 32, the coil spring 38 is additionally compressed to allow the head of the female post 34 to protrude away from the recess 50 in the femoral cap 48 to disengage and reposition the femoral cap teeth 66 from and into radial slots 68 of femoral member 20. The resulting independent rotation of femoral cap 48 causes a modification of the allowable angular excursion of pin 56 in control slot 58. In this manner, the range of flexion or extension may be adjustably set in any one of 15 degrees increments.

Upon a releasing of the additional axial compressive load applied to the head of screw 32 the coil spring 38 pulls the head of female post 34 back into recess 50. This securely maintains the fixed position of femoral cap 50 relative to femoral member 20, and therefore, the allowed arcuate excursion of arms 20, 22.

The tension in the elastic member 92 and hence the coincident extension force provided by the dynamic joint may be set and adjusted either prior to or after fastening the brace to the patient's limb. While locking cap 42 and screw 32 remain partially unscrewed, tibial cap 46 may be held by the peripheral edges of elastic member groove 90 (FIG. 7) and pulled axially toward locking cap 42 which additionally compresses coil spring 38. The axial motion of tibial cap 46 (FIG. 7) relative to tibial member 22 disengages teeth 84 from slots 86. The tension in the elastic member may then be increased (or decreased) by rotating tibial cap 46 in 30 degree increments such that the arcuate wrap of the elastic member 92 within groove 90 is increased (or decreased).

Once the desired preloaded therapeutic extension force is set, locking cap 42 is rotated in order to drive screw 32 into the female post 34. The rotation of locking cap 42 may be limited by either the maximum compression of coil spring 38 or the thread length of screw 32 and post 34. When fully tightened, locking cap 42 defines the secured position of dynamic joint caps 46 and 48, brace support members 20 and 22, the range of motion, and the range of the elastic member force.

Figure 11:
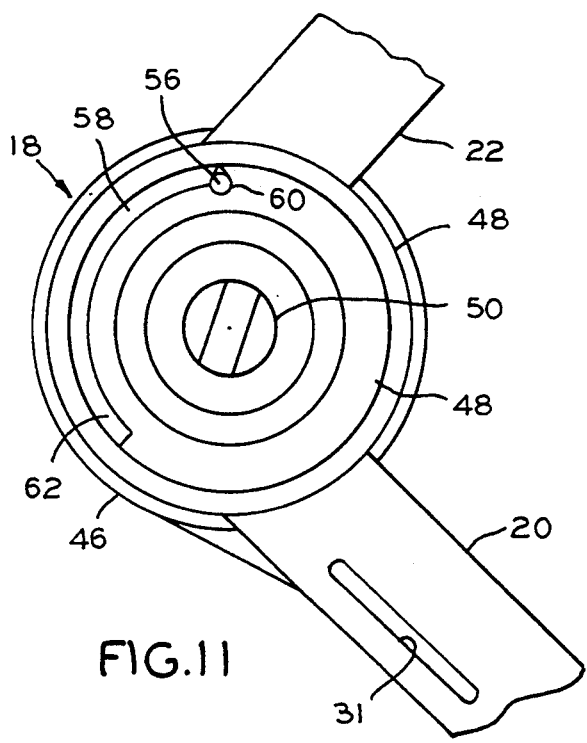
FIG. 11 is a partial plan view of the dynamic brace joint assembly shown at a set flexion limit with the femoral cap shown in a side elevation view.

FIG. 11 illustrates the brace joint from the medial face of femoral cap 48 as initially positioned at a set flexion limit. Floating stop pin 56 is shown in coincident contact with the flexion stop end 60 of pin control slot 58. At the set flexion limit, elastic member 92 experiences the maximum elongation due to its increased wrap within groove 90 of tibial cap 46, thereby providing the greatest extension force for the selected force range.

As the dynamic joint moves through the allowed range of motion, floating pin 56 rides through the allowed span of control slot 58 which guides pin 56 to the selected position fixed by end stop 62. As the joint rotates toward the extension limit, the force provided by elastic member 92 (which promotes and assists the extension) is gradually and continuously reduced down to the preloaded force condition reached at the set joint extension limit. If both of the dynamic joints of the brace are set at the same flexion limit, the resulting default extension limit is 180 degrees and floating stop pin 56 locks between extension limit stop 62 and the distal end of drop slot 60.

Each of the dynamic joints of the brace may be independently set to provide an extension limit in addition to the flexion limit. If a rigid brace is desired for applications such as post operative recovery, the brace joints may be set so that the flexion limit of one joint corresponds to the extension limit of the other joint resulting in a fixed position brace with no effective range of brace rotation.

Thus, the dynamic brace joint provides an incrementally adjustable range of pivoting motion with flexion and extension limits. The location of pin 56 in control slot 58 and the proximity of femoral cap 48 to the patient's limb, in conjunction with locking cap 42, inherently prevents a tampering with the selected range of motion while requiring no tools in order to set it. The continuous corrective load provided by the elastic member provides an increasing extension force during flexion of the limb joint. The quantifiable extension force may be easily selected or modified while in use, either by the patient or therapist. An appropriate extension force may be selected for a continuous prevention of a deteriorating contracture condition as well as for the purpose of rehabilitation and therapy.

Because the dynamic brace joint has a single axis revolute hinge providing only joint rotation, its use for the application of knee braces may be limited to non-ambulatory care of patients. The dynamic brace joint is, therefore, well suited for use with patients who are bedridden or who exhibit only a limited amount of mobility.

The planar profile of the brace support members facilitates its manufacture from flat stock. Likewise, the design of the femoral, tibial, and locking caps promotes proper joint assembly and further promotes the use of unique, corresponding sizes and spacing of complementary components. Moreover, the use of non-corrosive materials allows the dynamic brace joint to be laundered along with the accompanying soft goods comprising the splint or brace.

Those who are skilled in the art will readily perceive how to modify the invention. Therefore, the appended claims are to be construed to cover all equivalent structures which fall within the true scope and spirit of the invention.

The invention claimed is:

1. A dynamic brace joint for use in orthotic devices comprising:
   an upper brace support member;
   a lower brace support member;
   means for pivotally interconnecting said upper and lower members at their proximal ends;
   means for incrementally adjusting a range of pivotal motion of said interconnected upper and lower members;
   an elastic member for exerting a continuously applied dynamic force relative to said pivotal motion on said interconnected upper and lower members;
   means for adjusting the continuously applied force exerted by said elastic member;
   means for securely maintaining said dynamic force and said range of motion at a predetermined adjustment setting;
   wherein the means for adjusting the range of pivotal motion comprise a rotatable cap member; and
   wherein the means for securely maintaining comprise a spring mounted axially to said interconnected upper and lower members, said spring biasing said rotatable cap member toward the interconnected upper and lower members.

2. The dynamic brace of claim 1 wherein said upper and lower members are interconnected by a single dynamic revolute joint rotation.

3. The dynamic brace of claim 1 wherein said upper brace support member and said lower brace support member have means for coupling their terminal ends to an upper femoral cuff and a lower tibial cuff, respectively, by a splint or brace.

4. The dynamic brace joint of claim 1 wherein said range adjusting means may be set to define flexion and extension limits in a range of pivotal motion.

5. The dynamic brace of claim 1 wherein said range adjusting means releasably engages one of said brace members for locking said upper and lower members into a particular extension and flexion limit, said range adjusting means axially disengaging from said one member for adjusting the extension and flexion limits of said upper and lower members.

6. The dynamic brace of claim 5 wherein said range adjusting means comprises a floating stop pin and a rotatable cap member having an angular pin control slot, said stop pin traveling within said pin control slot for incrementally controlling the flexion and extension limits.

7. The dynamic brace joint of claim 6 wherein said angular pin control slot includes an extension stop end and an oppositely positioned flexion stop end.

8. The dynamic brace joint of claim 6 wherein said rotatable cap member comprises a plurality of radially oriented teeth which releasably engage a plurality of correspondingly oriented radial slots on said one member for locking said upper and lower members into the particular extension and flexion limit, the rotatable cap member being mounted to said interconnected members to be displaceable axially away from said one member when the axial spring is compressed, thereby disengaging said teeth from said slots of said one member to adjust the extension and flexion limits.

9. The dynamic brace joint of claim 6 wherein said stop pin is also in contact with one of a plurality of peripheral pin slots for additionally securing a stop pin within said angular pin control slot.

10. The dynamic brace of claim 1 wherein said force adjusting means releasably engages one of said brace members for applying a predetermined dynamic force on said upper and lower members, said force adjusting means axially disengaging from said one member for modifying the force.

11. The dynamic brace joint of claim 1 further comprising means for sequentially and pivotally mounting said range adjusting means, said interconnecting means, said upper and lower members, and said means for securely maintaining.

12. A dynamic brace joint for use in orthotic devices comprising:
   an upper brace support member;
   a lower brace support member;
   means for pivotally interconnecting said upper and lower members at their proximal ends;
   means for incrementally adjusting a range of pivotal motion of said interconnected upper and lower members;
   an elastic member for exerting a continuously applied dynamic force relative to said pivotal motion on said interconnected upper and lower members; and
   means for adjusting the continuously applied force exerted by said elastic member;

wherein said force adjusting means releasably engages one of said brace members for applying a predetermined dynamic force on said upper and lower member, said force adjusting means axially disengaging from said one member for modifying the force; and wherein said force adjusting means comprising an elastic member located on the periphery of a rotatable cap member, said elastic member wrapping around the periphery of said cap member to increase its tension as said cap member is rotated in one direction, and the tension in said cap member being decreased as it unwraps from the periphery of said cap member as said cap member is rotated in the opposite direction.

13. The dynamic brace of claim 12 wherein said rotatable cap member includes a plurality of radially extending teeth which releasably engage a plurality of corresponding cap slots in said one member for securely positioning said upper and lower members under a predetermined dynamic force, said teeth of said rotatable cap member disengaging from said slots of said one member as said rotatable cap member is axially moved away from said one member to adjust the predetermined dynamic force.

14. A dynamic brace joint for use in orthotic devices on a patient's limb comprising:
    an upper brace support member;
    a lower brace support member;
    means for pivotally interconnecting said upper and lower members at their proximal ends;
    means for incrementally adjusting the range of pivotal motion of said interconnected upper and lower members;
    a tensioning member for exerting a continuously applied dynamic force on said interconnected upper and lower members;
    means for adjusting the continuously applied force exerted by said tensioning member;
    means for securely maintaining said dynamic force and said range of motion at a predetermined setting; and
    means for mounting said brace joint on a patient's limb;
    wherein the adjusting means comprises
    a first cap rotatably mounted relative to said interconnected members, said first cap being displaceable axially away from said interconnected members and having a peripheral groove around the circumference thereof, said tensioning member being aligned with and at least partially received in the groove;
    a spring mounted against said first cap to bias said first cap against said one of said interconnected members;
    whereby more or less of the tensioning member is received in said groove when the spring is compressed and the first cap is axially displaced and rotated, thereby adjusting the continuously applied force.

15. The joint of claim 14 wherein each of said upper and lower brace support member is an elongated arm having a first pivot mount in said proximal end in order to partially form said pivotal interconnecting means, a circular pattern formed by one of equi-spaced slots or teeth, said circular pattern being centered on said first pivot mount, a second cap, said first and second caps having second pivot mounts cooperating with said first pivot mounts in order to further form said pivotal interconnecting means, each of said caps having a circular pattern formed by the other of said equi-spaced slots or teeth, said circular pattern on said caps being centered on said second pivot mount, whereby each of said caps may be connected in a selected angular orientation to an associated one of said support member by pressing said teeth into said slots.

16. The joint of claim 15 wherein one of said caps has an arcuate slot with an effective length selected by the angular orientation selected when said cap and an associated first of said support members are connected together, and means associated with said arcuate slot for limiting motion of said first pivot mount at the effective length of said arcuate slot.

17. A dynamic brace joint for use in orthotic devices on a patient's limb comprising:
    an upper brace support member;
    a lower brace support member;
    means for pivotally interconnecting said upper and lower members at their proximal ends;
    means for incrementally adjusting the range of pivotal motion of said interconnected upper and lower members;
    a tensioning member for exerting a continuously applied dynamic force on said interconnected upper and lower members;
    means for adjusting the continuously applied force exerted by said tensioning member;
    means for securely maintaining said dynamic force and said range of motion at a predetermined setting; and
    means for mounting said brace joint on a patient's limb;
    wherein each of said upper and lower brace support member is an elongated arm having a first pivot mount in said proximal end in order to partially form said pivotal interconnecting means, a circular pattern formed by one of equi-spaced slots or teeth, said circular pattern being centered on said first pivot mount, a pair of caps having second pivot mounts cooperating with said first pivot mounts in order to further form said pivotal interconnecting means, each of said caps having a circular pattern formed by the other of said equi-spaced slots or teeth, said circular pattern on said caps being centered on said second pivot mount, whereby each of said caps may be connected in a selected angular orientation to an associated one of said support member by pressing said teeth into said slots;
    wherein one of said caps has an arcuate slot with an effective length selected by the angular orientation selected when said cap and an associated first of said support members are connected together, and means associated with said arcuate slot for limiting motion of said first pivot mount at the effective length of said arcuate slot; and
    wherein the other of said caps has a peripheral groove around the circumference thereof, said other cap being associated with a second of said support members, an elongated elastic member having one end attached to said first support member, the other end of said elongated elastic member being attached to lie in said peripheral groove and wrap around at least part of the circumference of said other cap whereby the tension in said elastic member is selected by pre-wrapping said elastic member around a selected arcuate portion of said circumference before said other cap is connected to said second support member.

18. A dynamic brace joint for use in orthotic devices comprising:
- an upper brace support member;
- a lower brace support member;
- means for pivotally interconnecting said upper and lower members at their proximal ends;
- means for incrementally adjusting a range of pivotal motion of said interconnected upper and lower members;
- an elastic member for exerting a continuously applied dynamic force relative to said pivotal motion on said interconnected upper and lower members; and
- means for adjusting the continuously applied force exerted by said elastic member;
- means for securely maintaining said dynamic force and said range of motion at a predetermined adjustment setting;
- wherein the means for adjusting the range of pivotal motion comprise a rotatable cap; and
- wherein the means for securely maintaining comprise means for displaceably biasing said rotatable cap toward the interconnected upper and lower members.

19. A dynamic brace joint for use in orthotic devices on a patient's limb comprising:
- an upper brace support member;
- a lower brace support member;
- means for pivotally interconnecting said upper and lower members at their proximal ends;
- means for incrementally adjusting the range of pivotal motion of said interconnected upper and lower members;
- a tensioning member for exerting a continuously applied dynamic force on said interconnected upper and lower members;
- means for adjusting the continuously applied force exerted by said tensioning member;
- means for securely maintaining said dynamic force and said range of motion at a predetermined setting; and
- means for mounting said brace joint on a patient's limb; wherein the adjusting means comprises
- a first cap rotatably mounted relative to said interconnected members, said first cap being displaceable axially away from said interconnected members and having a peripheral groove around the circumference thereof, said tensioning member being aligned with and at least partially received in the groove;
- means for displaceably biasing said first cap against said one of said interconnected members;
- whereby more or less of the tensioning member is received in said groove when the first cap is axially displaced and rotated, thereby adjusting the continuously applied force.

20. A dynamic brace joint comprising:
- (a) a pair of members pivotally connected to each other to form a pivot axis;
- (b) a rotatable member having a peripheral groove around the edge thereof, the rotatable member being mounted to and axially displaceable from the pivotally connected members;
- (c) means for releasably securing the rotatable member in a fixed angular position relative to the pivotally connected members; and
- (d) a tensioning member having one end connected to one of the pivotally connected members, the tensioning member being aligned with and partially received in the groove;
- the tensioning member being adjustable by axially displacing and rotating the rotatable member to receive more or less of the tensioning member.

21. The dynamic brace joint of claim 20, wherein the means for releasably securing includes teeth radially arrayed on the surface of the rotatable member adjacent one of the pivotally connected members, slots in the one pivotally connected member adapted to receive the teeth, and means for displaceably biasing the rotatable member against the pivotally connected members to maintain the teeth in the slots.

22. A dynamic brace joint comprising:
- (a) a pair of members pivotally connected to each other to form a pivot axis;
- (b) a covering member having a peripheral groove around the edge thereof, the covering member being rotatably mounted to and axially displaceable from the pivotally connected members;
- (c) means for releasably securing the covering member in a fixed angular position relative to the pivotally connected members; and
- (d) a tensioning member having one end connected to one of the pivotally connected members, the tensioning member being aligned with and partially received in the groove;
- wherein the means for releasably securing include means for displaceably biasing said covering member toward the pivotally connected members.

* * * * *